United States Patent
Parramon

(10) Patent No.: US 9,867,994 B2
(45) Date of Patent: Jan. 16, 2018

(54) EXTERNAL POWERING OF IMPLANTABLE MEDICAL DEVICE DEPENDENT ON ENERGY OF PROVIDED THERAPY

(71) Applicant: Boston Scientific Neuromodulation Corporation, Valencia, CA (US)

(72) Inventor: Jordi Parramon, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/090,367

(22) Filed: Apr. 4, 2016

(65) Prior Publication Data

US 2016/0367822 A1    Dec. 22, 2016

Related U.S. Application Data

(60) Provisional application No. 62/181,834, filed on Jun. 19, 2015.

(51) Int. Cl.
*A61N 1/378* (2006.01)
*A61N 1/36* (2006.01)

(52) U.S. Cl.
CPC ....... *A61N 1/3787* (2013.01); *A61N 1/36125* (2013.01)

(58) Field of Classification Search
CPC .................................................. A61N 1/3787
USPC ........................................................ 607/61
See application file for complete search history.

(56) References Cited

U.S. PATENT DOCUMENTS

| | | | |
|---|---|---|---|
| 5,948,006 A | 9/1999 | Mann | |
| 6,275,737 B1 | 8/2001 | Mann | |
| 7,351,921 B1 | 4/2008 | Haller et al. | |
| 7,444,181 B2 | 10/2008 | Shi et al. | |
| 7,650,187 B2 * | 1/2010 | Gruber | A61N 1/3787 607/33 |
| 7,881,803 B2 | 2/2011 | Parramon et al. | |
| 8,335,569 B2 | 12/2012 | Aghassian | |
| 8,498,716 B2 | 7/2013 | Chen et al. | |
| 8,929,996 B2 | 1/2015 | Ginggen et al. | |

(Continued)

OTHER PUBLICATIONS

Invitation to Pay Additional Fees regarding corresponding PCT Application No. PCT/US2016/026150, dated Jul. 20, 2016.

(Continued)

*Primary Examiner* — Allen Porter, Jr.
(74) *Attorney, Agent, or Firm* — Lewis, Reese & Nesmith, PLLC

(57) ABSTRACT

An implantable medical device system includes an implantable medical device for providing stimulation therapy and two external power sources. A first external power source is used to power the implantable medical device when the stimulation therapy is low energy therapy. For example, the first external power device may be utilized to periodically recharge a battery in the implantable medical device. The second external power device may be utilized to power the implantable medical device when the stimulation therapy is high energy therapy. The second external power device may be a disposable patch that is affixed to a patient's skin to provide continuous power to the implantable medical device. The implantable medical device may communicate data to such a power device to cause it to adjust a strength of the charging field that it generates.

25 Claims, 9 Drawing Sheets

(56) References Cited

U.S. PATENT DOCUMENTS

| | | | |
|---|---|---|---|
| 9,002,445 B2 | 4/2015 | Chen | |
| 9,192,772 B1* | 11/2015 | Tsukamoto | A61N 1/3605 |
| 2002/0032471 A1* | 3/2002 | Loftin | A61N 1/37211 |
| | | | 607/61 |
| 2002/0183800 A1* | 12/2002 | Schmidt | A61N 1/08 |
| | | | 607/32 |
| 2007/0118180 A1* | 5/2007 | Ni | A61N 1/3627 |
| | | | 607/17 |
| 2009/0058361 A1* | 3/2009 | John | A61N 1/3785 |
| | | | 320/128 |
| 2010/0268309 A1 | 10/2010 | Parramon et al. | |
| 2010/0274312 A1 | 10/2010 | Alataris et al. | |
| 2011/0101790 A1* | 5/2011 | Budgett | A61M 1/127 |
| | | | 307/104 |
| 2012/0004708 A1 | 1/2012 | Chen et al. | |
| 2012/0283800 A1 | 11/2012 | Perryman et al. | |
| 2013/0018440 A1* | 1/2013 | Chow | A61N 1/3787 |
| | | | 607/61 |
| 2013/0066400 A1 | 3/2013 | Perryman et al. | |
| 2013/0079849 A1 | 3/2013 | Perryman et al. | |
| 2013/0165993 A1* | 6/2013 | Aghassian | A61N 1/36125 |
| | | | 607/59 |
| 2013/0253614 A1 | 9/2013 | Knifong | |
| 2013/0310901 A1 | 11/2013 | Perryman et al. | |
| 2014/0058480 A1 | 2/2014 | Perryman et al. | |
| 2014/0358194 A1 | 12/2014 | Vansickle et al. | |
| 2015/0080982 A1 | 3/2015 | Funderburk | |
| 2015/0360038 A1 | 12/2015 | Zottola et al. | |

OTHER PUBLICATIONS

International Search Report and Written Opinion regarding corresponding PCT Application No. PCT/US2016/026150, dated Sep. 28, 2016.

* cited by examiner

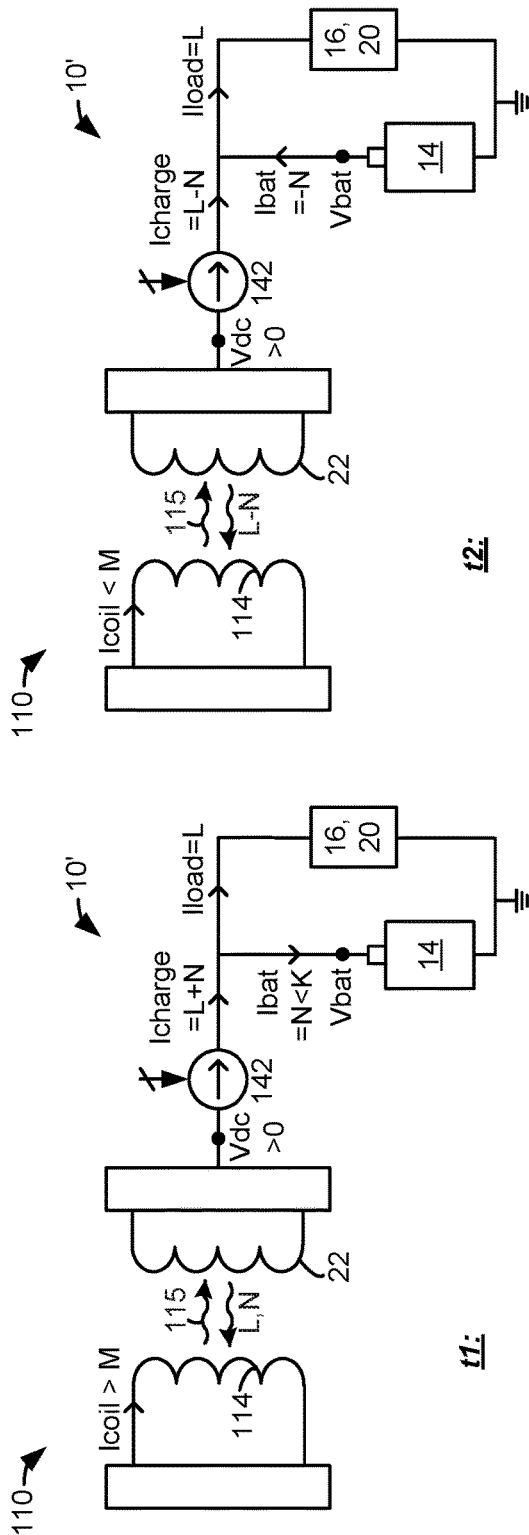
*Figure 7C*
*Figure 7D*
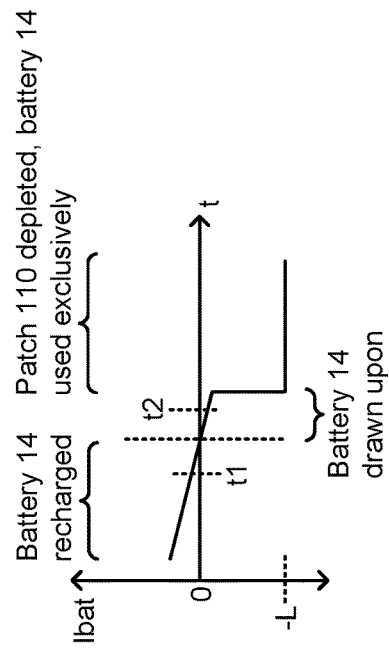
*Figure 7E*

EXTERNAL POWERING OF IMPLANTABLE MEDICAL DEVICE DEPENDENT ON ENERGY OF PROVIDED THERAPY

CROSS REFERENCE TO RELATED APPLICATIONS

This is a non-provisional patent application of U.S. Provisional Patent Application 62/181,834, filed Jun. 19, 2015, which is incorporated by reference in its entirety, and to which priority is claimed.

FIELD OF THE INVENTION

The present application relates to an implantable medical device (IMD), and to a system in which the IMD is differently powered depending on the therapy the IMD is providing.

BACKGROUND

Implantable stimulation devices generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, occipital nerve stimulators to treat migraine headaches, and other neural stimulators to treat urinary incontinence, sleep apnea, shoulder subluxation, etc. The present invention may find applicability in all such applications, although the description that follows will generally focus on the use of the invention in a microstimulator device system of the type disclosed in U.S. Patent Publ. No. 2010/0268309, which is incorporated herein by reference in its entirety. Despite being described in the context of a microstimulator device system, the invention can also be used in any implantable stimulator device system, such as a Spinal Cord Stimulator (SCS) used to treat lower back pain, such as is disclosed in U.S. Pat. No. 7,444,181, which is incorporated herein by reference in its entirety, for example. "Microstimulator" as used in the following should thus be understood as comprising any implantable stimulator.

Microstimulator devices typically comprise a small, generally-cylindrical housing which carries electrodes for producing a desired stimulation current. Devices of this type are implanted proximate to the target tissue to allow the stimulation current to stimulate the target tissue to provide therapy for a wide variety of conditions and disorders. A microstimulator usually includes or carries stimulating electrodes intended to contact the patient's tissue, but may also have electrodes coupled to the body of the device via a lead or leads. A microstimulator typically has two electrodes, although microstimulators can also have more than two electrodes in an array, such as is disclosed in U.S. Pat. No. 7,881,803, which is incorporated herein by reference in its entirety, for example. Microstimulators benefit from simplicity. Because of their small size, the microstimulator can be directly implanted at a site requiring patient therapy.

FIG. 1 illustrates in cross-section an exemplary implantable microstimulator 10 having only two electrodes 12a and 12b. As shown, the microstimulator 10 includes a power source 14 such as a battery, control circuitry (e.g., a microcontroller) 16, and various electrical circuitry 20 including stimulation circuitry for forming stimulation pulses at the electrodes 12a/b, and a coil 22. Stimulation pulses may be defined by a stimulation program (SP) stored in memory, which memory may be associated with either or both of the microcontroller 16 and the electrical circuitry 20. A stimulation program may define the amplitude, pulse width, and frequency of the pulses, or other parameters of the pulses, as explained further below.

Electrical components are integrated by a circuit board 24 and housed within a capsule 26, which is usually a thin, elongated cylinder, but may also be any other shape as determined by the structure of the desired target tissue 5, the method of implantation, and/or the number and arrangement of external electrodes 12a/b.

The battery 14 supplies power to the various components within the microstimulator 10, including power for providing the stimulation current sourced or sunk from the electrodes 12a/b as provided by circuitry 20. Battery 14 may be a primary battery, a rechargeable battery, a capacitor, or any other suitable power source.

The coil 22 is configured to receive and/or emit a magnetic field that is used to communicate with, and/or receive power from, one or more external devices that support the implanted microstimulator 10, examples of which will be described below. Such communication and/or power transfer may be transcutaneous (i.e., through a patient's tissue 5) as is well known. Transmitter/receiver circuitry may be coupled to coil 22, as explained further below.

The illustrated microstimulator 10 includes electrodes 12a/b on the exterior of the capsule 26. The electrodes 12a/b may be disposed at either end of the capsule 26 as illustrated, or placed along the length of the capsule. There may also be more than two electrodes arranged in an array, as described earlier. One of the electrodes 12a/b may be designated as a stimulating electrode, with the other acting as an indifferent electrode (reference node) used to complete a stimulation circuit, producing monopolar stimulation. Or, one electrode 12a/b may act as an anode while the other acts as a cathode, producing bipolar stimulation. Electrodes 12a/b may alternatively be located at the ends of short, flexible leads. The use of such leads permits, among other things, electrical stimulation to be directed to targeted tissue(s) a short distance from the surgical fixation of the bulk of the microstimulator 10. In one example, microstimulator 10 may be built as disclosed in U.S. Pat. No. 7,351,921, which is incorporated herein by reference in its entirety.

Turning to FIGS. 2A and 2B, the microstimulator 10 is illustrated as implanted in a patient's tissue 5, and further shown are various external components that may be used to support the implanted microstimulator 10. An external controller 30 may be used to control and monitor the microstimulator 10 via a bidirectional communication link 35. Communication on link 35 can occur via magnetic inductive coupling between the external controller's coil 32 and the microstimulator's coil 22 as is well known. Typically, the magnetic field on link 35 is modulated, for example with Frequency Shift Keying (FSK) modulation or the like, to encode transmitted data. For example, data telemetry via FSK can occur around a center frequency of fc=125 kHz, with a 129 kHz signal representing transmission of a logic '1' bit and 121 kHz representing a logic '0' bit.

The external controller 30 is generally similar to a cell phone for example and includes control circuitry (e.g., a microcontroller) 34, a battery 36, and a port such as a USB port 38 which is formed in the controller's hand-holdable and portable housing 40. The external controller 30 can include a user interface including buttons 42 and a display 44, and may include other user interface elements such as a speaker (not shown). The various electronic components may be integrated in the external controller 30 using a circuit board 46.

An external charger 50 provides power to recharge the microstimulator's battery 14 (FIG. 1). Such power transfer occurs by energizing a coil 52 in the external charger 50, which produces a magnetic field comprising link 55, which may occur with a different frequency (f2=80 kHz) than data communications on link 35. This magnetic field 55 energizes the coil 22 in the microstimulator 10, which is rectified, filtered, and used to recharge the battery 14, as explained further subsequently. Link 55, like link 35, can be bidirectional to allow the microstimulator 10 to report status information back to the external charger 50, again as explained subsequently. For example, once control circuitry 16 in the microstimulator 10 detects that the battery 14 is fully charged, its coil 22 can signal that fact back to the external charger 50 so that charging can cease.

The external charger 50 generally comprises a hand-holdable and portable housing 54, in which are contained a battery 56 for powering the charger's electronics, including circuitry 58, which may include a microcontroller 58 for example. The external charger 50's circuitry may be integrated on one or more circuit boards 60, as explained for example in U.S. Pat. No. 9,002,445, which is incorporated herein by reference in its entirety. The external charger 50 may have a relatively simple user interface, including for example only an on/off button 62 to begin production of the magnetic field comprising link 55, and may additionally include an indicator, such as a Light Emitting Diode (LED) 64 or a speaker (not shown). Although not depicted, the external charger 50 may include a display as well.

In other examples, data communication and charging functionality may be integrated in a single external device or system. For example, and although not illustrated, data communication and charging may be integrated within a single housing, as disclosed in U.S. Pat. No. 8,335,569, which is incorporated herein by reference in its entirety. Alternatively, the charging coil 52 can comprise an assembly coupleable by a cable to port on the housing of the controller, which controller can comprise the external controller 30 as disclosed in U.S. Pat. No. 8,498,716, which is incorporated herein by reference in its entirety, or which controller is specifically dedicated to charging functionality without implicating implant data communications. In either case, integration of the external charger with an external communicator generally allows charging functionality to benefit from the external controller's provision of an improved user interface, in particular its display.

A further external device supporting the microstimulator 10 is shown in FIG. 2B, which comprises a well-known clinician programmer 70, and which may be as described in U.S. Patent Application Publication 2015/0360038, which is incorporated herein by reference in its entirety. A clinician programmer 70 is generally used by a clinician to control and monitor a patient's microstimulator 10 in a clinical setting. For example, clinician programmer 70 can be used after implantation to initially program the microstimulator 10 with a stimulation program that is most effective for the patient, although the patient may later modify this program in certain respect using his external controller 30. The clinician programmer 70 may also be used for routine check-ups to adjust the stimulation program or monitor microstimulator 10 operation.

The clinician programmer 70 typically comprises a personal computer 72, which may be portable, such as a laptop or tablet computer. The computer 72 includes a display 74 with a graphical user interface 80 rendered by clinician programmer (CP) software 78 executed by control circuitry 76 of the computer 72. As the computer 72 may not inherently have means to communicate directly with the implant, the clinician programmer 70 can include a communication head 82, sometime called a "wand." The communication head 82 includes an antenna coil 88 similar in function to the coil 32 in the external controller 30, and capable of communicating with the coil 22 in the microstimulator via link 95 (e.g., by FSK). The communication head 82 is coupled to a port 86 of the computer 72, which may comprise a USB port for example. If necessary, the communication head 82 may also include modulation and demodulation circuitry, although not shown.

Due to its small size, a microstimulator such as 10 is useful in providing neurostimulation in many locations within the human body and for many different therapeutic purposes, such as those already mentioned. However, the inventor notes that due to its relatively small size, the battery 14 within the microstimulator 10 is also necessarily small, and hence of low capacity. For example, battery 14 may only have a capacity of 20 mAh for example. Depending on the therapy the microstimulator must provide, a battery 14 of this capacity may not allow the microstimulator to operate for a sufficiently long period of time between charging sessions provided by the external charger 50. This disclosure addresses this problem by providing a system in which external power is provided differently for the microstimulator 10 depending on the therapy the microstimulator is providing.

BRIEF DESCRIPTION OF THE DRAWINGS

FIGS. 7C and 7D show modifications to FIG. 7B in which the circuitry both slightly recharges and draws upon the microstimulator's battery when the patch is used, and FIG. 7E shows such use of the battery graphically.

DETAILED DESCRIPTION OF THE INVENTION

Figure 3:
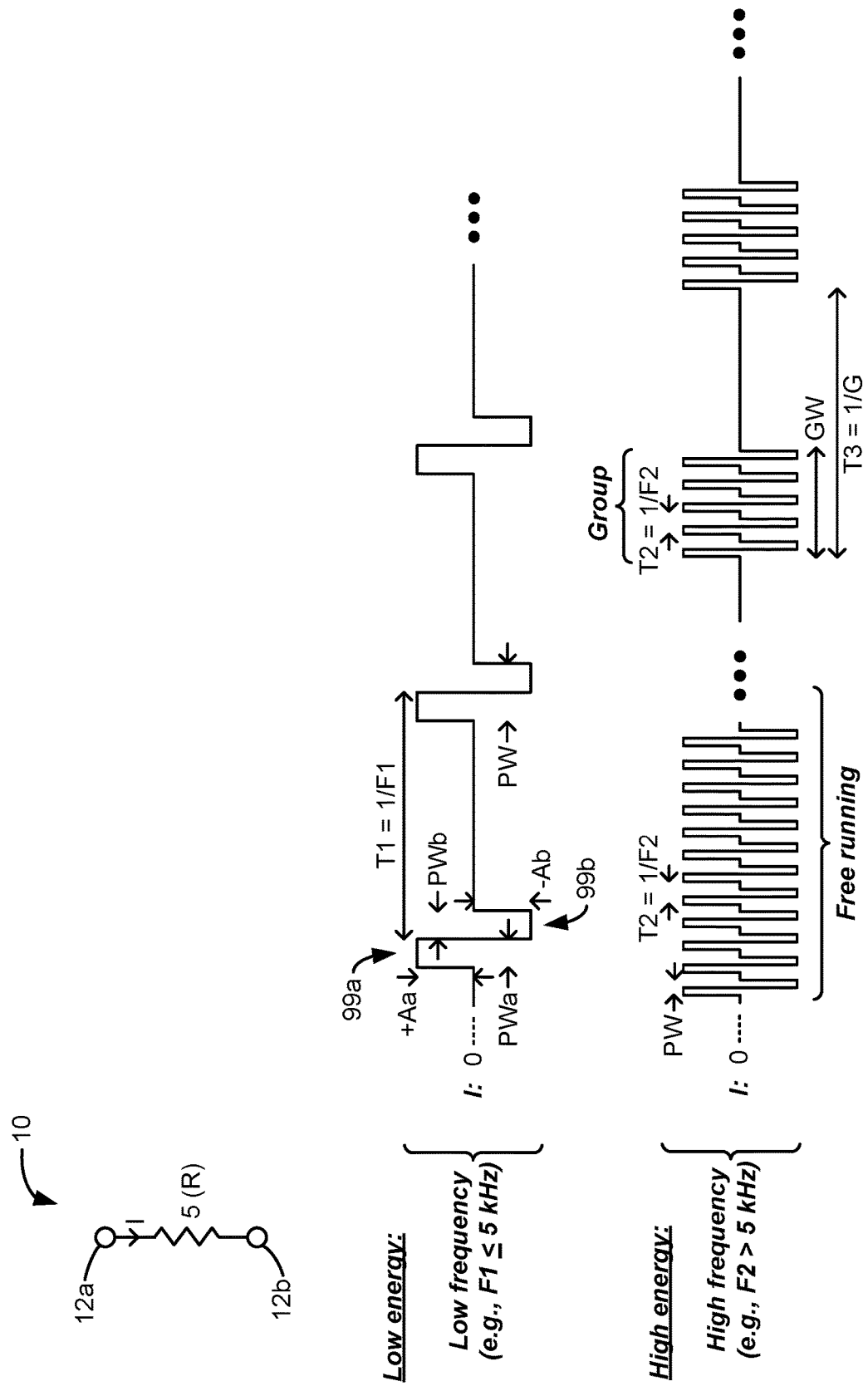
FIG. 3 shows various types of stimulation therapy the microstimulator may provide, including low energy and high energy stimulation, in accordance with the prior art.

As discussed earlier, the rechargeable battery 14 within a microstimulator 10 is small and of relatively low capacity. This means that the battery 14 may need to be frequently recharged using the external charger 50 depending on the therapy the microstimulator 10 is providing and how much energy is required. Examples of different therapies are shown in FIG. 3, which comprise various types of stimulation pulses that pass through a patient's tissue 5 from electrode (anode) 12a to electrode (cathode) 12b.

The top row of pulses illustrates conventional stimulation therapy, in which pulses are issued with an amplitude A, a pulse width PW, and a frequency F1. The pulses as shown are biphasic, meaning that an initial pulse 99a is followed by an opposite-polarity pulse 99b of equal but opposite charge (i.e., |Aa|*PWa=|−Ab|*PWb). Using a biphasic pulse is typical in a neurostimulator (although not required) as it promotes charge recovery from any capacitances (either inherent or provided for DC blocking) that may be present in the current path, I. In the example shown, the amplitudes (Aa, Ab) and pulse widths (PWa, PWb) are equal in the pulse phases 99a and 99b, although the opposite-polarity pulse 99b can have different amplitudes and pulse widths while still meeting the condition of equal charge with the first pulse phase 99a. The use of biphasic pulses in a neurostimulator and its benefits are well-known.

The frequency F1 of the pulses in the top row can be 5 kHz or less, which can be characterized as low frequency, and as such the pulse widths PW can be equal to 200 microseconds or more. However, the use of high frequency stimulation has also been promoted as useful in the neurostimulation arts, as shown in the bottom row of FIG. 3. In this example, pulses (again illustrated as biphasic, but not strictly necessary) are issued at a higher frequencies F2, which may be greater than 5 kHz, and are typically less than 1 MHz. More specifically, F2 may be greater than or equal to 10 kHz and less than or equal to 150 kHz. The pulse widths PW used during high frequency stimulation may be less than 200 microseconds. High frequency stimulation has been touted as providing pain relief in a Spinal Cord Stimulator (SCS) application for example without inducing paresthesia. See, e.g., U.S. Patent Application Publication 2010/0274312, which is incorporated herein by reference in its entirety.

Depending on the patient's therapeutic needs, such high frequency pulses may be free running, as shown to the left of the bottom row, or issued in groups with periods of no stimulation in between, as shown to the right of the bottom row. Such groups of pulses may comprise a group width (GW) containing a plurality of pulses, which group widths may in one example equal the pulse widths (PW) provided in low frequency therapies. The groups of pulses themselves may issue with a frequency of G, which may generally equal the pulse frequencies (F1) provided in low frequency therapies.

Which type of therapy (low or high frequency; free running or in groups) will provide the best therapy for a given patient is difficult to know at the time of microstimulator 10 implantation. Thus, microstimulator 10 preferably provides the ability to issue stimulation pulses according to any of these regimes. However, the inventor realizes that while it is beneficial for a microstimulator 10 to be programmable to provide a wide spectrum of therapies such as those illustrated in FIG. 3, the therapy implemented in a given microstimulator 10 for a given patient has a significant effect on the power drawn within the microstimulator 10, and thus has a significant effect on the rechargeable battery 14.

Generally speaking, low frequency stimulation will be low energy, and draw less power from the rechargeable battery 14. Low energies resulting from low frequency therapies can be due to several factors. For example, the pulse widths PW may be small in comparison to the period (T1=1/F1) at which the low frequency pulses are issued (i.e., the pulses have a low duty cycle), or the pulses may not transition that frequently. Transitions in the shape of the produced pulses require use of switching of circuitry in the microstimulator 10, and (as is known) power draw is generally proportional to the rate at which switching of circuitry occurs.

By contrast, high frequency stimulation may require higher energies. This may be because high frequency pulses are active (PW) for a higher amount of time compared to their periods (T2=1/F2), and thus the pulses have a high duty cycle, when free running for example. Plus, high frequency stimulation involves higher switching rates, even if groups of high frequency pulses are used.

In sum, high frequency simulation can require significantly higher energies than low frequency stimulation, which will more quickly deplete the low-capacity battery 14. Higher energy stimulation will in turn require more frequent charging of the battery 14 by the external charger 50. If high frequency stimulation (e.g., 10 kHz free running) is used with a microstimulator 10 and battery 14 of the type disclosed earlier, it is estimated that the battery will become depleted after only a few hours of usage. This means that the microstimulator patient would need to use the external charger 50 several times a day to keep recharging the microstimulator's battery 14, which obviously isn't convenient for the patient.

Characterizing neurostimulation therapy as low or high energy can also be premised on factors other than the frequency of stimulation. For example, and although not depicted, one therapy may simply require pulses with low amplitudes (Aa, Ab) and/or low pulse widths (PWa, PWb) thus resulting in low energy stimulation, while another therapy may require pulses with higher amplitudes or pulse widths resulting in high energy stimulation.

Regardless of the reason that a given stimulation therapy may be referred to as low or high energy, and regardless of how one may quantify the dividing line between low and high energy stimulation, the inventor proposes a system in which external power is differently provided to the microstimulator depending on the type of therapy the microstimulator is providing to the patient.

Figure 1:
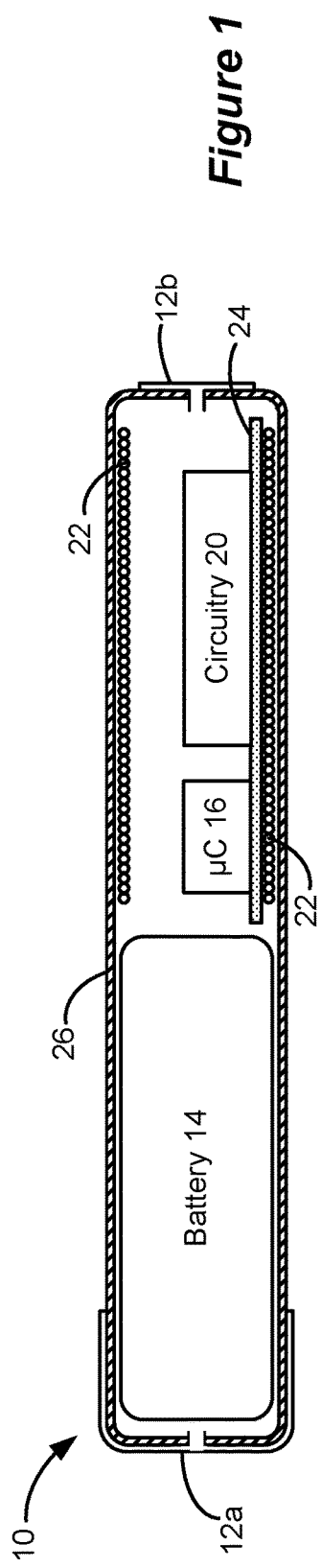
FIG. 1 shows an implantable stimulator, in particular a microstimulator, in accordance with the prior art.
Figure 2A:
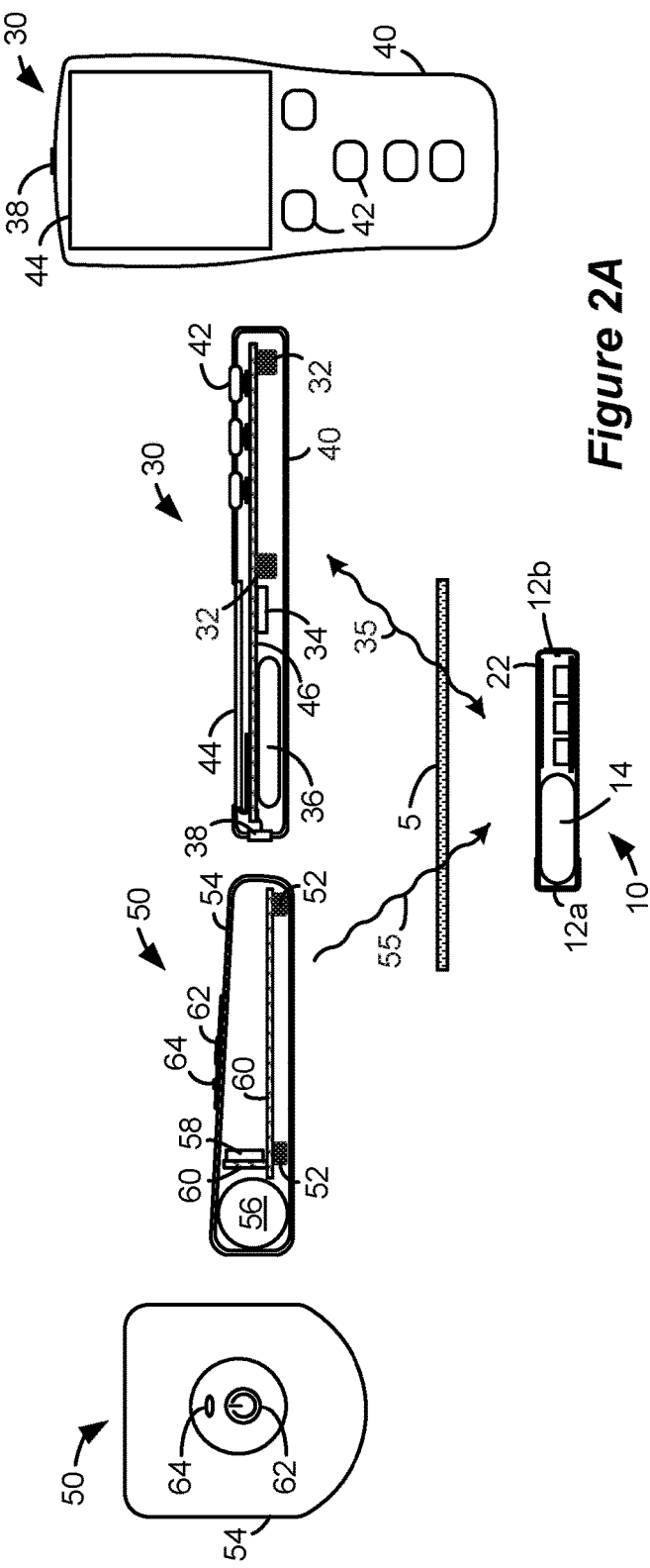
FIGS. 2A-2B show a microstimulator as implanted in a patient, as well as external devices that support the microstimulator, including an external charger and external controller (FIG. 2A), and a clinician programmer (FIG. 2B), in accordance with the prior art.
Figure 2B:
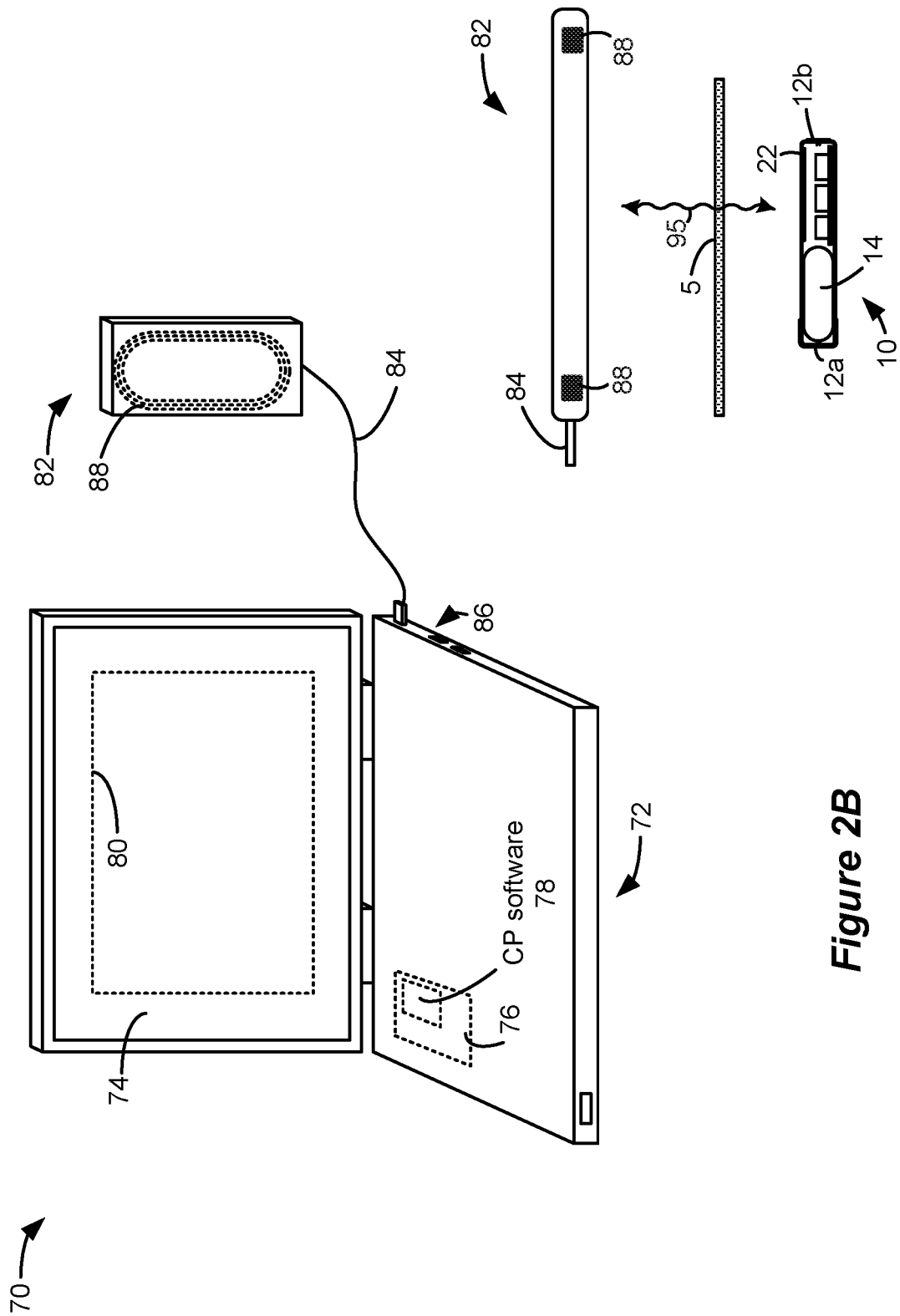
Figure 4:
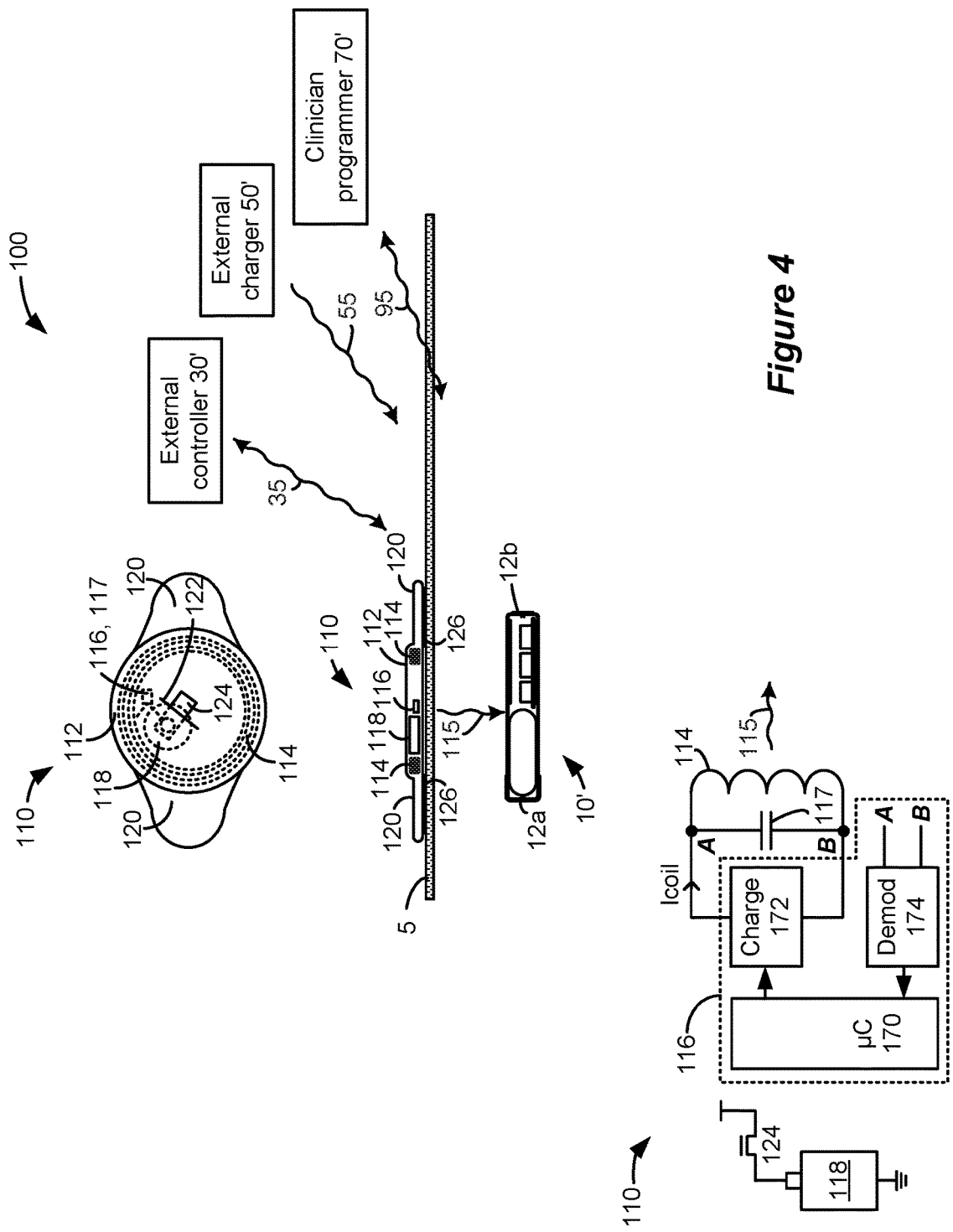
FIG. 4 shows an improved system useable with a potentially-improved microstimulator and potentially-improved external devices, and including a power patch for providing continuous power to the microstimulator, in accordance with examples of the invention.

FIG. 4 shows an improved system 100, which can include as before a microstimulator 10', an external controller 30', an external charger 50', and a clinician programmer 70'. Depending on how the system 100 is implemented, these devices may be as described earlier in legacy neurostimulator systems (i.e., 10, 30, 50, and 70; FIGS. 2A and 2B) although new element numerals are used as these components may also be modified to include additional functionality as described subsequently. As should be clear from the description below, not all of external devices 30', 50', and 70' may be necessary in useful embodiments of the system 100.

A possible (but not strictly necessary) component new to system 100 is a power patch 110. The power patch 110 is used to provide continuous power to the microstimulator 10' when the therapy required by the microstimulator is of high energy—e.g., when high frequency stimulation is used by the patient. The power patch 110 is preferably a cheap and simple external component, and is preferably also disposable. As shown, the patch 110 includes a battery 118 (preferably of a flat configuration, such as a coin-shaped battery), a charging coil 114, a capacitor 117 for tuning the frequency of the magnetic field in conjunction with the coil 114, and circuitry 116. Although the coil 114 and capacitor 117 are shown in FIG. 4 connected in parallel to create a resonant tank circuit, they may be connected in series as well, as is well known.

Preferably, the patch 110 can alter the strength of the magnetic field 115 it produces using feedback from the microstimulator 10', as discussed further below, and so circuitry 116 as illustrated in FIG. 4 supports such functionality. Specifically, circuitry 116 includes a demodulator 174 for decoding data wirelessly received from the microstimulator 10'; control circuitry (such as a microcontroller) 170 for interpreting such data; and charging circuitry 172 for setting the strength of the AC current (Icoil) that will flow through the patch's coil 114, and hence the strength of the magnetic field 115 it produces. While such magnetic field 115 adjustments are desirable for the reasons discussed below, circuitry 116 isn't strictly necessary in all embodiments of the patch 110. Instead, the coil 114 and capacitor 117 can be connected to the battery 118 to provide a non-adjustable continuous magnetic field 115.

As noted, the patch 110 may be used to provide continuous power (via magnetic field 115) to the microstimulator 10' when high energy therapy is being provided, and preferably only provides enough power as needed by the microstimulator 10' to operate to provide the high energy therapy. Thus, patch 110 may not provide excess power to recharge the microstimulator's battery 14, although it may charge the battery slightly as described further below. Even though magnetic field 115 is used when the microstimulator 10' is providing high energy therapy, this field 115 may be of lower power than the magnetic field 55 produced by the external charger 50'. This is because the external charger 50' will still be used as in legacy systems to recharge the battery 14 when the microstimulator 10' is to provide low energy therapy to the patient. In this regard, it is preferred that the power of magnetic field 55 be relatively high during the limited periods when the external charger 50' is being used to recharge the battery 14 so that it may be recharged as quickly as possible. The frequency of the magnetic field 115 produced by the patch 110 may be tuned to the same frequency (e.g., 80 kHz) as the magnetic field 55 produced by the external charger 50', both of which may be generally tuned to match the natural resonance of the coil 22 in the microstimulator 10' for efficient energy transfer. While the power supply to the microstimulator 10' has been described as occurring via inductive coupling between the external charger 50' or the patch 110 and the microstimulator 10', such power transfer could also occur at high-frequency RF (e.g., >3 MHz) or microwave frequencies over links 55 and 115. In such an arrangement, coils 22, 52, and 114 may be replaced by antennas. Like energy transfer via inductive coupling, the strength of the electromagnetic wave generated by the external charger 50' may be greater than the strength of the electromagnetic wave generated by the continuous power device when power transfer occurs at high-frequency RF (e.g., >3 MHz) or microwave frequencies.

As noted, the patch 110 is preferably (but not necessarily) disposable, and thus may generally resemble a band aid in structure. The housing 112 of the patch 110 may be made for example of a soft plastic material between which the coil 114 and other electronic components are sandwiched. If necessary, wings 120 outside of the area of the electronics may be included to promote affixation to the patient's skin above the implanted location of the microstimulator 10', and adhesive 126 may be positioned under the wings 120. Alternatively, wings 120 may not be needed, and adhesive 126 can instead be placed underneath the electronics of the patch 110. It should be noted that while use of an adhesive 126 is preferred to affix the patch 110 at the location of the microstimulator 10', this is not strictly required and other means of positioning the patch 110 can be used as well. Although not shown, the patch 110 electronics can be supported within the housing 112 by a substrate, preferably a flexible substrate such as formed of Kapton for example. As noted above, continuous power transfer may occur via high-frequency RF or microwave power transfer rather than inductive coupling. In such a case, the continuous power supply may be provided from a device other than patch 110, such as a device that is not affixed to the patient's skin proximate to the implanted location of the microstimulator 10'.

The housing 112 may additionally include a slit 122 though which protrudes an insulating strip 124. The strip 124 when pulled out can be used to connect the patch's battery 118 to the remainder of the electronics, thus beginning production of the magnetic field 115. Due to its preferably simple construction, note that the patch 110 preferably contains no user interface elements other than what is necessary to begin generation of the magnetic field 115 (e.g., the strip 124). Once the patch 110 starts generating the magnetic field 115, it is contemplated that the field 115 will thereafter be continuously produced until the battery 118 is depleted, at which time a new patch 110 would need to be affixed to the patient. Alternatively, the battery 118 may be replaceable in the patch 110, thus allowing the patch to be re-used.

Figure 5A:
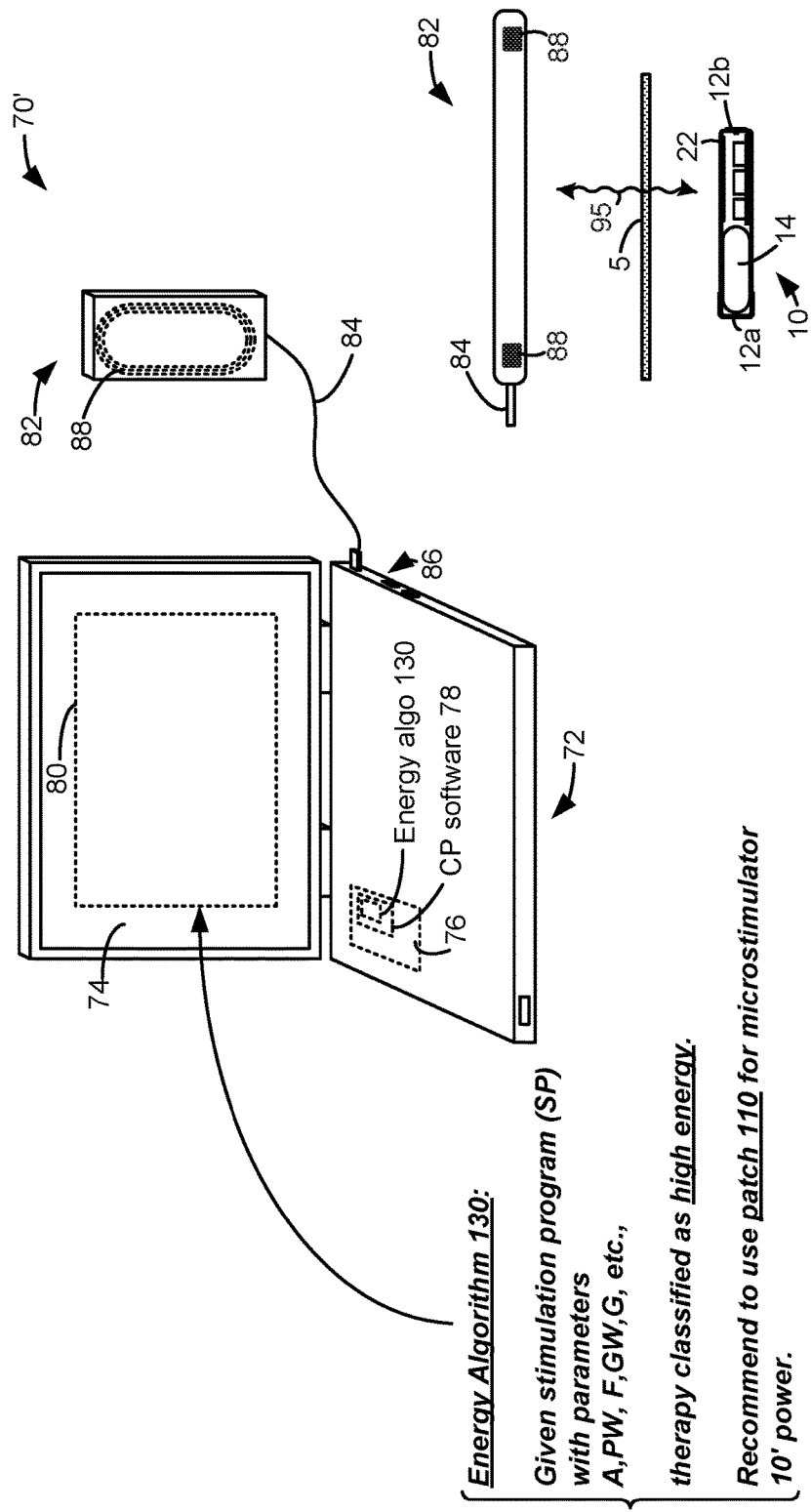
FIGS. 5A and 5B show use of an energy algorithm in external data communication devices to determine whether stimulation therapy is low or high energy, and which external power device should be used with the microstimulator, in accordance with examples of the invention.
Figure 5B:
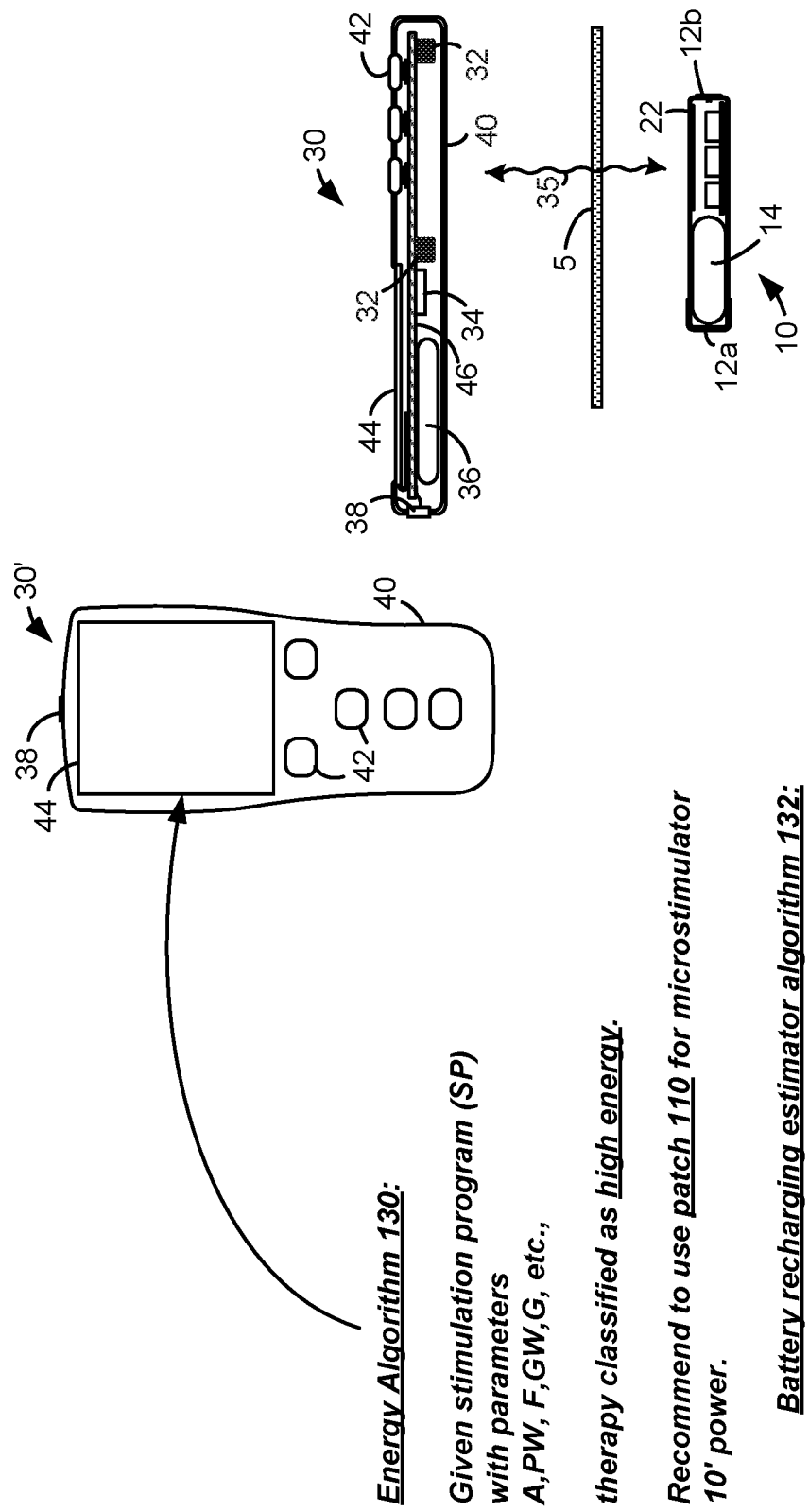

Whether stimulation therapy provided by the microstimulator 10 is low or high energy, and thus whether the external charger 50' or patch 110 is best indicated for use with a patient's microstimulator 10', can be determined in different manners in system 100 as illustrated in the following figures. In FIGS. 5A and 5B, such determination is made in the external data communication devices.

For example, FIG. 5A illustrates use of the clinician programmer 70' to determine the relative energy of stimulation in accordance with an energy algorithm 130. As noted earlier, the clinician programmer can be used to transmit a stimulation program (SP) to the microstimulator 10', which program comprises a number of stimulation parameters (A, PW, etc.) defining the pulses to be provided at the electrodes 12a and 12b. The CP software 78, in addition to providing the user interface for interaction with the microstimulator 10', can also include an energy algorithm module 130 for assessing the energy involved in the particular stimulation program, for example by assessing the stimulation parameters of the stimulation program.

The energy algorithm 130 can determine whether the stimulation program is high or low energy in different ways. For example, the energy algorithm 130 may simply inquire about the frequency (F) of the stimulation pulses, and determine that the therapy is high energy if the frequency is greater than or equal to a threshold (e.g., if F≥5 kHz). Otherwise (if F<5 kHz), the energy algorithm 130 can consider the stimulation therapy to be low energy.

The energy algorithm 130 may also perform a more complicated mathematical analysis of the stimulation parameters in the stimulation program. For example, the energy algorithm 130 can assess energy involved in stimulation by effectively computing the amount of charge of the stimulation pulses as a function of time. This can involve multiplying the pulse amplitude (A), pulse width (PW), and pulse frequency (F), or if the pulses are issued in groups, then additionally multiplying these parameters by the group width (GW) and group frequency (G). Of course, such calculations can also include differences in amplitudes (Aa, Ab) or pulse widths (PWa, PWb) used in different pulse phases 99a and 99b (FIG. 3). In any event, if the charge-per-time is greater than or equal to a given threshold, then the energy algorithm 130 can consider the stimulation therapy to be high energy. Otherwise, the energy algorithm 130 can consider the stimulation therapy to be low energy. Other manners of setting the boundary between low and high energy can be used as well. For example, the energy algorithm 130 may consider more than just the energy inherent in the pulses, and may consider background energy consumed by other supporting electronics in the microstimulator 10' as well, such as the microcontroller 16 and the stimulation circuitry 20.

As FIG. 5A shows, the results of the energy algorithm 130 can be rendered on the graphical user interface 80 of the computer 72, and can inform the clinician whether the prescribed therapy comprises high or low energy. In accordance with this determination, the energy algorithm 130 can also recommend the external power source that should be used with the patient's microstimulator 10'—e.g., the patch 110 if the energy is high and continuous power is indicated, or the external charger 50' if the energy is low for intermittent charging of the battery 14.

The energy algorithm 130 can further include computations relevant to the low/high energy determination, such as a battery recharging estimator algorithm 132. This algorithm 132 can display estimations for the clinician regarding how frequently the patient would be expected to need to recharge the battery 14 in his microstimulator 10' given the stimulation program were the external charger 50' intermittently used, as well as how long each of these charging sessions would be expected to take. For example, FIG. 5A shows that for the illustrated high energy determination, battery 14 recharging would take place six times for 75 minutes each. This would likely be an inconvenient situation for the patient, as they might need to use the external charger 50' almost eight hours a day. The continuously-powered disposable patch 110 would thus provide a better solution, as a given patch 110 may be engineered to last for weeks. Battery recharging estimator algorithm 132, and how it determines estimated charging frequencies and durations, is disclosed in U.S. Patent Application Publication 2014/0358194, which is incorporated herein by reference in its entirety. Note that only information regarding battery recharging estimations 132 may be displayed to the clinician without a particular external power source recommendation, leaving it to the clinician to decide whether the external charger 50' or patch 110 should be used.

Although not illustrated, energy algorithm 130 can provide further information of interest. For example, if high energy use is indicated, energy algorithm 130 might make suggestions concerning how therapy could be changed to make it lower energy such that the external charger 50' might be required instead of the patch 110. Such modification could involve suggesting adjustment to various stimulation parameters to arrive at estimated charging frequencies and durations (132) that are not inconvenient for the patient. (Of course, such adjustments to the therapy may not suitably provide the patient therapeutic relief from his symptoms, and so convenient use of the external charger 50' may simply not be possible).

FIG. 5B illustrates use of the energy algorithm 130 as stored and executed in the external controller 30' by its control circuitry 34 (FIG. 2A). This is useful as the external controller 30' can be used by the patient to change the stimulation program or its individual stimulation parameters, which can have an effect on the energy the microstimulator 10' will require. Thus, as the patient changes therapy using the external controller 30', the energy algorithm 130 can re-determine whether the energy is high or low, and make recommendations to the patient concerning the best external device (the external charger 50' or the patch 110) to provide power to his microstimulator 10'. Reviewing the information the energy algorithm 130 provides can comprise a selectable menu option in the user interface of the external controller 30'.

In either of FIGS. 5A and 5B, it is assumed that the clinician programmer 70' (FIG. 5A) and the external controller 30' (FIG. 5B) knows the stimulation program the microstimulator 10's is running by virtue of sending it to the microstimulator 10. However, if this is not known, the stimulation program and its parameters can be telemetered from the microstimulator 10' to these devices via links 95 and 35 so that it can be assessed by the energy algorithm 130 as described above.

Further, the external data communication device 70' or 30' upon making the energy determination can transmit that determination to the microstimulator 10' to inform it of the external power device 50' or 110 that the microstimulator 10' should expect to receive. Although not depicted, this alternative may be useful to allow the microstimulator 10' to configure itself for either continuous powering via the patch 110, or intermittent powering via the external charger 50' to charge the battery 14.

Figure 6:
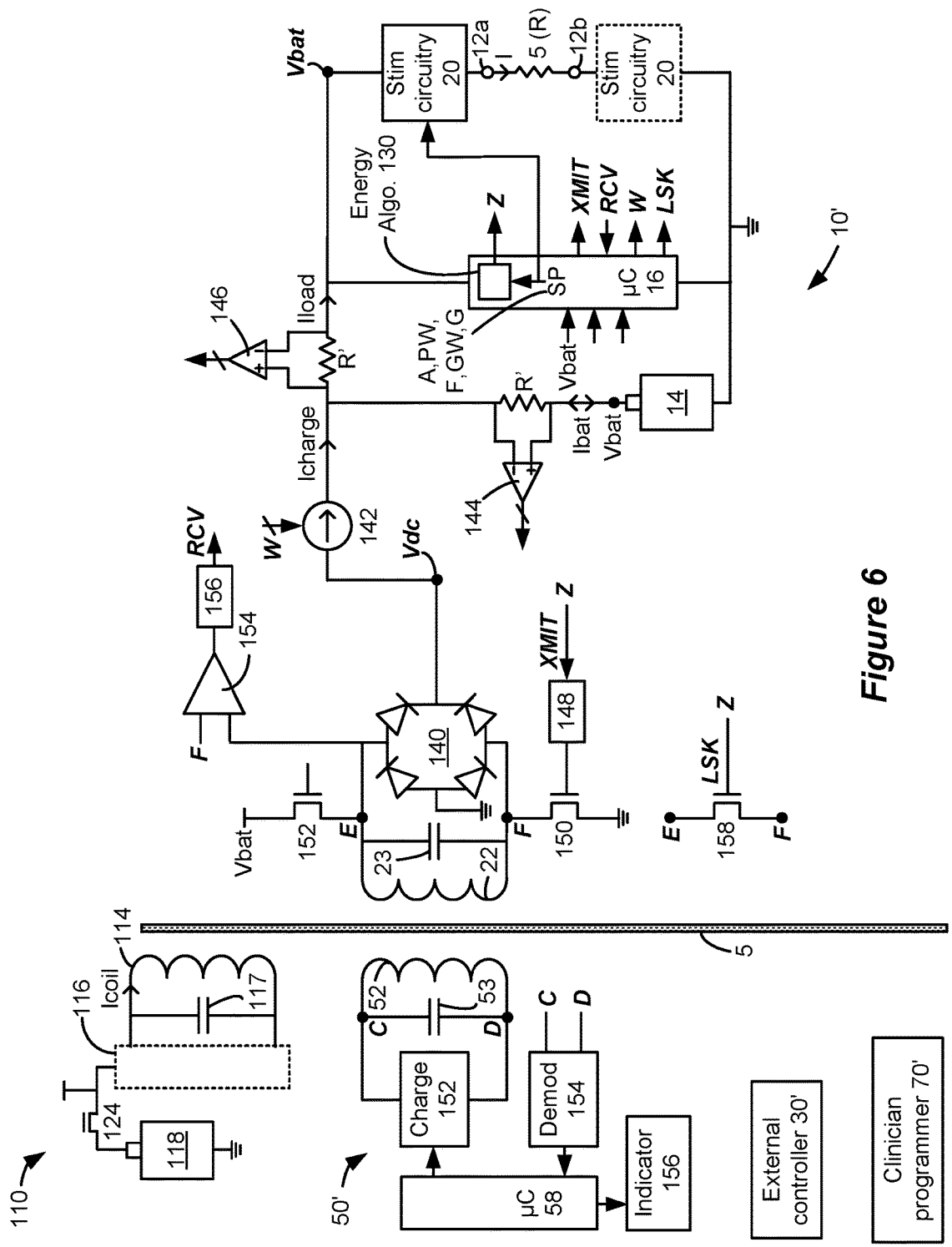
FIG. 6 shows use of the energy algorithm in the microstimulator, and communication of its energy determination to the external data communication devices and/or the external charger, in accordance with examples of the invention.

Energy algorithm 130 can also be programmed into the microstimulator 10', as shown in FIG. 6, which additionally shows one example of circuitry that can be used in the microstimulator 10', which circuitry is briefly described. Receipt of power is described first.

Regardless which external power device is used—the external charger 50' or the power patch 110—a magnetic field (55 or 115) is received at the microstimulator's coil 22 which resonates in conjunction with its tuning capacitor 23 (e.g., at 80 kHz). This AC resonance is passed to a rectifier 140 to produce a DC voltage, Vdc. This voltage Vdc is used both to charge the microstimulator's battery 14 via current Ibat (e.g., if external charger 50' is being used), and to provide the power necessary for microstimulator 10' operation via current Iload, as explained further below. Either or both of Ibat and Iload can be measured using differential amplifiers 144 and 146 respectively, which infer these currents by assessing a voltage drop V that they cause across a low-resistance resistor R' (I=V/R'). Ultimately, the measured Ibat and Iload are digitized and provided to the microstimulator's microcontroller 16 as one or more control signals.

Preferably, but not necessarily, Ibat and Iload are controllably provided by a programmable current source 142 powered by Vdc, which outputs a controlled current Icharge in accordance with one or more control signals W determined by the microstimulator's microcontroller 16 in accordance with its needs at the moment, as described further below.

The stimulation program (SP) operating in the microstimulator 10' is stored in memory associated with the microcontroller 16, and can be provided to stimulation circuitry 20 to produce pulses at electrodes 12a and 12b as prescribed by its stimulation parameters (A, PW, etc.). Stimulation circuitry 20 can be configured in several different manners, and may comprise a voltage or current source. Additionally, stimulation circuitry 20 may be associated with both of electrodes 12a and 12b to allow both active sourcing and sinking of current to and from the patient's tissue 5 (R).

The stimulation program is also provided to the energy algorithm 130, which makes an assessment of its stimulation parameters and whether the therapy is to be considered low or high energy in any of the manners described above. The energy algorithm 130 issues one or more energy determination signals Z indicating this determination (e.g., Z='0' if energy low; Z='1' if energy is high). Z may then be telemetered to any of the external devices to inform the clinician or patient which external power source to use—i.e., the external charger 50' if Z='0', or the patch 110 if Z='1'.

Telemetry of energy determination signal Z (and other microstimulator data) can occur in different manners, which manners can be affected by the external device to which the signal is to be sent. As illustrated, telemetry circuitry in the microstimulator 10' uses the same coil 22 used for reception of the magnetic field 55 or 115 from the external power devices 50' or 110. Data to be transmitted from the microstimulator 10' (XMIT) is provided from the microcontroller 16 to a modulator 148, which toggles a transistor 150 coupled between an end of the coil 22 and ground. Transistor 152 coupled between the other end of the coil 22 and Vbat is closed to selectively allow a current to flow through the coil 22 as controlled by transistor 150.

The selectively-controlled current flowing through coil 22 generates a magnetic field modulated (e.g., via FSK) with data representing energy determination signal Z, which can be received at the clinician programmer 70' or external controller 30' via bi-directional communication links 95 and 35. Those devices upon receiving Z can in turn display at least whether the energy consumption in the microstimulator 10' is considered low ('0') or high ('1'), and preferably may also then recommend the external power source (50' or 110) to be used with the microstimulator, as shown in FIGS. 5A and 5B. Other information such as battery recharging estimations (132; FIGS. 5A & 5B) may not be displayed, although such data may also be computed by the energy algorithm 130 in the microstimulator 10' and telemetered to the clinician programmer 70' or external controller 30' as well. What is important is that data indicative of the relative energy of the stimulation therapy is determined in the microstimulator 10' and telemetered to an external device to assist in informing as to the type of external power device that is most beneficially used.

It may not be practical for the microstimulator 10' to transmit energy determination signal Z (or other energy-indicative data) to the clinician programmer 70' or external controller 30' when an external power source 50' or 110 is providing its magnetic field 55 or 115. Instead, telemetry and power reception may need to be time-multiplexed at the microstimulator's coil 22 to avoid interference.

Telemetry circuitry in the microstimulator 10' may also transmit energy-indicative data from the energy algorithm 130 to the external charger 50', which can also indicate to the patient the results of the energy determination, and hence whether the external charger 50' presently being used is appropriate or whether the patch 110 should be used. Such means of telemetry from the microstimulator 10' to the external charger 50' can comprise Load Shift Keying (LSK). As is known, LSK involves modulating the impedance of the coil 22 in the microstimulator 10' with data to be transmitted to the external charger 50' (e.g., Z), which causes decodable perturbations in the magnetic field 55 the external charger 50' produces. Microstimulator 10' thus includes LSK circuitry for this purpose, represented as a transistor 158 capable of selectively shorting both ends of the coil 22 together in accordance with the energy-indicative data. (LSK circuitry may also selectively short both ends of the coil 22 to ground). Telemetry of data from an implantable medical device to an external charger via LSK is discussed further in U.S. Patent Application Publication 2015/0080982, which is incorporated herein by reference in its entirety.

In any event, energy-indicative data determined by the energy algorithm 130 in the microstimulator 10' is telemetered to the external charger 50', where it is demodulated 154 and provided to the control circuitry 58 (such as a microcontroller). The microcontroller 58 may then indicate the data to the patient via an indicator 156, which as mentioned earlier can comprise one or more LEDs 64 (FIG. 2A) or a speaker. For example, the external charger 50' could illuminate a particular LED 64, or illuminate LED 64 with a particular pattern or color, if the energy algorithm 130 in the microprocessor 10' determined that the energy in the stimulation therapy was high, and hence that use of the continually-powered patch 110 is instead warranted. Particular tones or audible patterns from a speaker in the external controller 50' could indicate this as well. Indicator 156 may also comprise a display should one be associated with the external charger 50', see, e.g., U.S. Pat. Nos. 8,335,569 and 8,498,716 discussed above. Conversely, indicator 156 may indicate that external charger 50' is appropriate to externally power the microstimulator—i.e., to use the external charger 50' to recharge the microstimulator's battery 14.

If energy algorithm 130 resides in the microstimulator 10', its results may be telemetered to any of the external devices (30', 50', 70') by different means. For example, the microstimulator 10' can include another coil or other antenna distinct from the coil 22 used to receive power from an external source (50' or 110). Such additional antenna may comprise a short range, far-field Radio Frequency (RF) antenna. Such a non-magnetic induction antenna may allow the energy-indicative (or other) data to be transmitted to an external device having a compliant antenna without interference even during provision of the magnetic field from the external power sources (55, 115). This may enable the microstimulator 10' to communicate (e.g., to an external device) information regarding its utilization of energy received from an external power device in real time while the energy is being received as described in greater detail below.

Figure 7B:
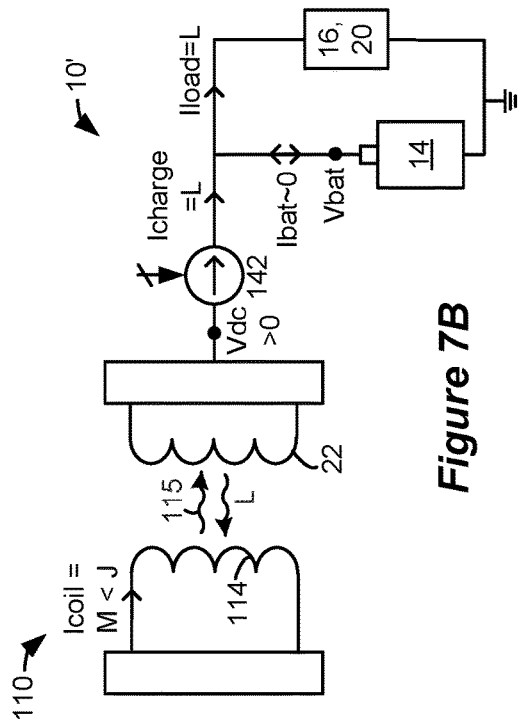
FIG. 7B shows circuitry and currents involved in use of a patch in a high energy stimulation therapy scenario.
Figure 7A:
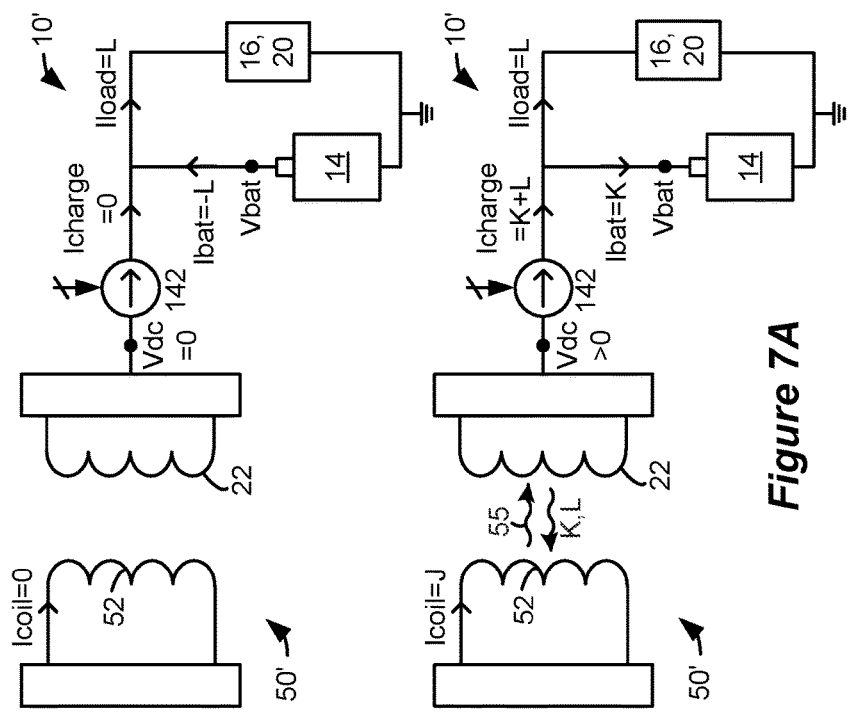
FIG. 7A shows circuitry and currents involved in use of an external charger in a low energy stimulation therapy scenario.

The microstimulator 10' can be powered by either the external power device 50' or the patch 110, and further details are shown in FIGS. 7A and 7B respectively. As noted earlier, the patch 110 can alter the strength of the magnetic field 115 it produces using feedback from the microstimulator 10', and such feedback can be telemetered to the patch 110 during production of its magnetic field 115. As discussed above, such telemetry can be performed in several different ways, although LSK would be preferred as this can occur during production of the magnetic field 115.

Use of the external charger 50' to power the microstimulator 10' in a low energy scenario is shown in FIG. 7A. The top of FIG. 7A shows operation of the microstimulator 10' between charging sessions when the external charger 50' is off (Icoil=0) or is simply not present. Because no magnetic field 55 is generated Vdc in the microstimulator 10' will be zero, as will Icharge. As such, the load current Iload needed for operation of the microstimulator 10' must be entirely drawn from the battery 14. Thus, if Iload=L, Ibat=−L.

The bottom of FIG. 7A shows the battery 14 being recharged by the external charger 50' during a charging session. The external charger 50' thus produces a magnetic field 55 by virtue of passing current J through its coil 52 (Icoil=J). This magnetic field 55 is received at the microstimulator's coil 22, and Vdc is therefore higher than zero (Vdc>0), and thus the current source 142 is powered and able to supply a current Icharge. Because the microstimulator 10' still operates and thus draws a load current of Iload=L, and if it is assumed that the battery 14 will be charged with a current of Ibat=K, then the current source 142 must output at least the sum of these two currents, i.e., Icharge=K+L.

The microcontroller 16 in the microstimulator 10' can monitor whether both of the battery current and the load current are sufficient by monitoring the differential amplifiers 144 and 146 respectively. If either current is insufficient, the microstimulator can provide feedback to the external charger 50' so that it may adjust the strength of the magnetic field 55 in a closed loop fashion. For example, the microstimulator 10' can telemeter the values of the measured battery current and load current to the external charger 50', or can simply telemeter data indicating that the magnetic field needs to be increased. In response, the external charger 50' can increase the strength of the magnetic field by increasing the current through its coil (to a value greater than J).

FIG. 7B shows use of the patch 110 to provide continuous power to the microstimulator 10' in a high energy scenario. Because the patch 110 will be used continuously to power the microstimulator's load, the battery 14 in the microstimulator is generally not used, although such use can also be slight as explained further below. In this scenario, the magnetic field 115 produced by the patch 110 need not be as high of a power as when the external charger 50' is used during a charging session to recharge the battery 14, because the battery current Ibat can be essentially zero. The patch 110 instead merely needs to provide enough power to generate Iload=L for the load. The lower strength magnetic field 115 is represented by a current drawn through the patch's coil 114 (M) that is less than that used in the external charger 50, i.e., Icoil=M<J. Note that using a lower current in the patch 110 generally extends it longevity. Closed loop control is further used with the patch 110, which is more critical as the patch's battery 118 (FIG. 118) would generally be much lower than the capacity of the battery 56 (FIG. 2A) in the external charger 50', and is not rechargeable.

While the microstimulator's battery 14 may not be needed in a high energy scenario involving use of the patch 110, it is preferable that the battery 114 still be useable to a certain extent. This is useful for example to continue to provide the patient stimulation therapy if a first patch 110 has been depleted and before a second patch 110 can be reapplied, with the battery 14 being used to power the load in between use of the two patches (even if only for a small time). This is shown in FIGS. 7C and 7D. FIG. 7C shows use of the patch 110 earlier in its lifetime (at t1). In this instance, a small current N is used to slightly recharge the battery 14, which current preferably recharges the battery at a slower rate than when the external charger 50' is used, i.e., Ibat=N<K. In this way, the patch when it is newer can ensure that the battery 14 in the microstimulator 10' is slowly charged and will not deplete, and thus will be available to provide stimulation therapy when a patch 110 is not present. By closed loop control, the microstimulator 10' can inform the patch to produce a slightly higher magnetic field 115, meaning use of a current in the patch's coil 114 that is higher than when the battery charging current is essentially zero. Thus, comparing FIG. 7B and FIG. 7C, it is seen that the patch in FIG. 7C uses a slightly higher current in its coil 114 (Icoil>M) than when the battery current is zero (Icoil=M).

FIG. 7D shows use of the patch 110 later in its lifetime (at t2). In this instance, it may be desirable to start using the battery 14 to power the load slightly, as the patch 110 may be at risk of depleting. Thus, the battery current equals a slightly negative current, Ibat=−N. This means the patch 110 need only produce an even smaller magnetic field 115 (i.e., Icoil<M), which again can be effected by feedback. Eventually the patch 110 will deplete, and the battery 14 must then supply all of the power to the load of the microstimulator 10', i.e., Ibat=−L, similar to the scenario depicted at the top of FIG. 7A. FIG. 7E graphically explains use of the patch to both slightly recharge and slight draw upon the microstimulator's battery 14.

Information regarding the use of energy received from an external power device (e.g., external charger 50' or patch 110) by the microstimulator 10' may be transmitted from the microstimulator 10' to an external device. For example, the values of Icharge, Ibat, Iload, Vdc and Vbat may be transmitted to external controller 30' or clinician programmer 70'. Such communications may occur while energy is being received via the coil 22—e.g., the information may be communicated via an antenna or coil other than the coil 22 as described above. As such, the information may provide a substantially real time view of the utilization of energy by the microstimulator 10'. The energy utilization information may be presented to a patient or clinician on a user interface of an external device such as the external controller 30' or the clinician programmer 70'. For example, the energy utilization information may be presented on a diagram that is similar to the implanted portion (i.e., right side) of the diagrams in FIGS. 7A through 7D. Such a diagram may illustrate the direction and magnitude of the currents Icharge, Ibat, and Iload and the values Vdc and Vbat to provide an intuitive illustration of the current energy usage of the microstimulator 10'.

While the invention herein disclosed has been described by means of specific embodiments and applications thereof, numerous modifications and variations could be made thereto by those skilled in the art without departing from the scope of the invention set forth in the claims.

What is claimed is:

1. A system, comprising:
   an implantable medical device for providing stimulation therapy;
   a first external power device;
   a second external power device; and
   an external data communication device that is configured to characterize, based on one or more parameters of the stimulation therapy, the stimulation therapy as high energy therapy or low energy therapy, wherein the stimulation therapy is characterized as high energy therapy when its relative energy is greater than a threshold and low energy therapy when its relative energy is less than the threshold, wherein the first external power device is used to provide power to the implantable medical device when the stimulation therapy is characterized by the external data communication device as low energy therapy, and wherein the second external power device is used to provide power to the implantable medical device when the stimulation therapy is characterized by the external data communication device as high energy therapy.

2. The system of claim 1, wherein the first external power device is used to periodically recharge a battery in the implantable medical device.

3. The system of claim 1, wherein the second external power device is used to continuously power the implantable medical device.

4. The system of claim 1, wherein the second external power device is a disposable patch that is configured to be affixed to a patient's skin above an implanted location of the implantable medical device.

5. The system of claim 1, wherein the first and second external power devices provide power to the implantable medical device via inductive coupling.

6. The system of claim 5, wherein a first magnetic field generated by the first external power device is of higher power than a second magnetic field generated by the second external power device.

7. The system of claim 1, wherein the first and second external power devices comprise antennas that are configured to provide power via high frequency RF or microwave power transfer.

8. The system of claim 7, wherein power transfer occurs at a frequency greater than 3 megahertz.

9. The system of claim 1, wherein the external data communication device is configured to execute an energy algorithm to characterize the stimulation therapy as high energy therapy or low energy therapy based on the one or more parameters of the stimulation therapy.

10. The system of claim 9, wherein the external data communication device is a clinician's programmer that is configured to communicate the one or more parameters of the stimulation therapy to the implantable medical device.

11. The system of claim 9, wherein the external data communication device is an external controller that is configured to communicate the one or more parameters of the stimulation therapy to the implantable medical device.

12. The system of claim 9, wherein the characterization is displayed on a user interface of the external communication device.

13. The system of claim 9, wherein the energy algorithm provides an estimation of a recharge frequency and a recharge duration for a battery of the implantable medical device using the first external power device.

14. A method, comprising:
receiving, by control circuitry of an external communication device, one or more parameters of stimulation therapy to be provided by an implantable medical device;
characterizing, using the control circuitry, the stimulation therapy as high energy therapy or low energy therapy based on the one or more parameters, wherein the stimulation therapy is characterized as high energy therapy when its relative energy is greater than a threshold and low energy therapy when its relative energy is less than the threshold;
using the first external power device to provide power to the implantable medical device when the stimulation therapy is characterized as low energy therapy; and
using the second external power device to provide power to the implantable medical device when the stimulation therapy is characterized as high energy therapy.

15. The method of claim 14, wherein the first external power device is used to periodically recharge a battery in the implantable medical device.

16. The method of claim 14, wherein the second external power device is used to continuously power the implantable medical device.

17. The method of claim 14, wherein the second external power device is a disposable patch that is configured to be affixed to a patient's skin above an implanted location of the implantable medical device.

18. The method of claim 14, wherein the first and second external power devices provide power to the implantable medical device via inductive coupling.

19. The method of claim 18, wherein a first magnetic field generated by the first external power device is of higher power than a second magnetic field generated by the second external power device.

20. The method of claim 14, wherein characterizing the stimulation therapy as high energy therapy or low energy therapy comprises executing an energy algorithm.

21. The method of claim 20, wherein the external communication device is a clinician's programmer that is configured to communicate the one or more parameters of the stimulation therapy to the implantable medical device.

22. The method of claim 20, wherein the external communication device is an external controller that is configured to communicate the one or more parameters of the stimulation therapy to the implantable medical device.

23. The method of claim 20, wherein the energy algorithm provides an estimation of a recharge frequency and a recharge duration for a battery of the implantable medical device using the first external power device.

24. The method of claim 14, wherein the stimulation therapy comprises a plurality of pulses, and wherein characterizing the stimulation therapy as high energy therapy or low energy therapy comprises determining, using the control circuitry, whether a frequency of the pulses exceeds a frequency threshold.

25. The method of claim 14, wherein characterizing the stimulation therapy as high energy therapy or low energy therapy comprises determining, using the control circuitry, whether an amount of charge delivered by the stimulation therapy in a given time period exceeds the threshold.

* * * * *